United States Patent

Cuzzato

[11] Patent Number: 5,841,006
[45] Date of Patent: *Nov. 24, 1998

US005841006A

[54] PROCESS FOR PREPARING PENTAFLUOROETHANE

[75] Inventor: Paolo Cuzzato, Treviso, Italy

[73] Assignee: Ausimont S.p.A., Milan, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 755,823

[22] Filed: Nov. 26, 1996

[30] Foreign Application Priority Data

Nov. 28, 1995 [IT] Italy .................. MI95A2484

[51] Int. Cl.⁶ .................................... C07C 19/08
[52] U.S. Cl. ............................ 570/163; 570/170
[58] Field of Search ..................... 570/163, 170

[56] References Cited

U.S. PATENT DOCUMENTS

| | | |
|---|---|---|
| 5,087,329 | 2/1992 | Felix . |
| 5,345,014 | 9/1994 | Cuzzato .................. 570/163 |
| 5,346,595 | 9/1994 | Clemmer et al. . |
| 5,453,551 | 9/1995 | Lacroix et al. . |

FOREIGN PATENT DOCUMENTS

| | | |
|---|---|---|
| 0 508 631 | 10/1992 | European Pat. Off. . |
| 0 569 832 A1 | 11/1993 | European Pat. Off. . |
| 0 569 832 B1 | 11/1993 | European Pat. Off. . |
| WO 92/02476 | 2/1992 | WIPO . |

*Primary Examiner*—Gary Geist
*Assistant Examiner*—Jean F. Vollano
*Attorney, Agent, or Firm*—Finnegan, Henderson, Farabow, Garrett & Dunner, L.L.P.

[57] ABSTRACT

Process for preparing pentafluoroethane (125) containing amounts of 115 lower than 0.02% by weight wherein pentafluoroethane is obtained by a dismutation process of tetrafluorochloroethane $CF_3CHClF$ (HCFC-124) in gaseous phase in the presence of a chrome oxide catalyst ($CR_2O_3$) supported on a $AlF_3$ support, wherein one operates at temperatures from 140°–180° C. for contact times comprised between 15–30 seconds, from >180° C. to 240° C. for contact times between 5 to 15 seconds, from >240° C. to 260° C. for contact times between 1 to 5 seconds, from >260° to 300° C. for contact times between 0.1 to 1 second.

7 Claims, No Drawings

PROCESS FOR PREPARING PENTAFLUOROETHANE

The present invention relates to a process for preparing pentafluoroethane (HFC-125).

More particularly it relates to a process for preparing pentafluoroethane containing very low amounts of 1-chloropentafluoroethane (CFC-115), generally lower than 0.02% by weight, more preferably lower than 0.01%.

It is well known that fluorocarbons containing chlorine, the so called chlorofluorocarbons (CFC) cannot be utilized any longer according to international rules since they have dangerous effects both on the ozone layer in the atmosphere and/or owing to the greenhouse effect.

For many applications the CFC have had up to now, we can mention refrigerating mixtures, the use as foaming and spraying agents, wherein CFC are used alone or in admixture with each other, one tries to find substitutes not containing chlorine or containing chlorine contemporaneously with hydrogen atoms in the molecule, the so called hydrofluorocarbons and chlorofluorohydrocarbons respectively.

One of the CFC substitutes which is employed for refrigerating mixtures is the so called 125 which is a hydrofluorocarbon.

There are various processes known in the art for preparing 125, however what is required by an industrial plant is a simplified process which combines to high yields small amounts of undesired compounds, such as for instance chlorofluorocarbons which form as reaction by-products and which are to be eliminated from 125.

It is necessary to note that it the by-products are easily separable, no problem from the industrial point of view arises since it is sufficient a distillation column associated to the main plant of production of 125.

It is to be noticed that for the applications especially in the field of refrigerating mixtures at low temperatures it would be desirable that 125 had a very low content of 115, generally of about 100 ppm (0.01%). See for instance EP patent 612709 which corresponds to U.S. Pat. No. 5,453,551.

The separation of 115 from 125 by fractional distillation is extremely difficult and the purity indicated in the European patent mentioned above is almost impossible to be obtained in industrial plants. See for instance U.S. Pat. No. 5,087,329. In this patent moreover it is described a distillation to be capable of separating 115 from 125 mixtures containing 115 by addition of a third component among which for instance a chlorofluorohydrocarbon.

Various industrial processes for purifying 125 from 115 are described in the art.

For instance in EP 508631 it is described the reduction of 115 by the employment of metal hydrides to convert 115 into 125 in liquid phase. In this process the maximum conversions are about of 60%.

Another separation process by multistage distillation to remove 115 from 125 is described in U.S. Pat. No. 5,346,595. However the maximum purity obtained is 99.8%, therefore far higher than the limits desirable to be reached.

Another method which is described is the fluorination of 115 with HF to perfluoroethane (116) in the presence of chrome-based catalysts, 116 is successively separated by distillation from 125. See for instance EP patent 612709.

The drawback of all these processes described in the art resides in that an additional unit must be added to the industrial process for preparing 115, therefore with plant drawbacks and additional production costs.

The need was therefore felt to have available a process allowing to obtain directly from the 125 production plant a final product containing small amounts of 115, lower than 0.02% by weight without the need of additional operations.

It has been unexpectedly found that it is possible to obtain 125 with the small amounts of 115 indicated above if one operates with the process described hereinunder.

An object of the present invention is a process for preparing pentafluoroethane (125) containing amounts of 115 lower than 0.02% by weight wherein pentafluoroethane is obtained by a dismutation process of tetrafluorochloroethane $CF_3,CHClF$ (HCFC-124) in gaseous phase in the presence of a chrome oxide catalyst ($Cr_2O_3$) supported on a support comprising $AlF_3$, said support having a content in fluorine corresponding to at least 90% by weight of $AlF_3$ determined on the total weight of the support, wherein one operates at temperatures: from 140°–180° C. for contact times comprised between 15–30 seconds, from >180° to 240° C. for contact times between 5 to 15 seconds, from >240° to 260° C. for contact times between 1 to 5 seconds, from >260° to 300° C. for contact times between 0.1 to 1 second. One preferably operates in the range from 160° C. to 260° C., more preferably from 180° C. to 240° C.

In the preferred ranges, 125 is obtained with the indicated purities and with a content of 115 even lower than 0.005% by weight. In practice in the dismutation process of the invention, 124 is transformed into 125 and 123 and other by-products, the reaction product 125 is separated by distillation from 123 and from other by-products and is already ready to be utilized in the refrigerants field since the amounts of 115 contained therein are lower than the limits indicated above.

In this way the additional phases described in the processes of the art to separate 115 from 125 are avoided.

The catalyst of the present invention comprises $Cr_2O_3$ supported on $AlF_3$ according to methods well known in the art.

A preferred method comprises the support impregnation phases with an aqueous solution of a trivalent chrome salt, drying and then submitting the so impregnated support to an activation treatment with air or nitrogen, at temperatures from 200° to 600° C., but preferably from 350° to 500° C.

The preferred support is 100% by weight $AlF_3$, preferably in the gamma and/or beta form.

$AlF_3$ can also contain the delta form, generally up to 30% by weight.

The content of $Cr_2O_3$ in the supported catalyst generally ranges from 1 to 15% by weight, determined as Cr on the catalyst.

The catalyst of the invention is particularly suitable to be utilized in fluid bed plants.

The following examples are given for illustrative purposes but are not limitative of the scope of the present invention.

EXAMPLE 1

A catalyst comprising $Cr_2O_3$ on $AlF_3$ suitable to be utilized in a fluidized bed was prepared by impregnation of the granular $AlF_3$ support (mixture of the beta, gamma and/or delta phases having a surface area of 25–30 $m^2/g$, a fluorine content of about 95% of the theoric value) with an aqueous solution of $CrCl_3$, in a ratio of 492 g of $CrCl_3.6H_2O$ for kg of $AlF_3$.

The so obtained catalyst was dried in stove at 20° C. for several hours, then was introduced in an Inconel 600 tubular reactor having a diameter of 50 mm, equipped with porous septum and electrically heated.

Successively it was heated to 400° C. and treated for 10 hours with an air flow of 100 Nl/hour.

The content in chromium of the catalyst was 8% by weight. 100 cc (133 g) of the so prepared catalyst are placed in the above mentioned reactor. Then at the temperature of 260° C., 225 g/hour of HCFC-124 are fed by performing a contact time of 5 seconds.

The products are analysed by gaschromatography and contain:
125: 35.8% by moles; 124: 36.5% by moles;
123: 27.1% by moles; others: 0.6% by moles.

115 in 125, after separation of 125 from the obtained products, is lower than the detection limit, i.e. below 0.005% by weight.

EXAMPLE 2

Example 1 was repeated by using a contact time of 2.5 seconds by doubling the 124 feeding.

The products are analysed by gaschromatography and contain:
125: 23.9% by moles; 124: 56.9% by moles;
123: 18.7% by moles; others: 0.5% by moles.

115 in 125 is below the limit of 0.005% by weight.

EXAMPLE 3

800 cc of the catalyst of Ex. 1 are placed in the reactor of the previous examples and 530 g/hour of HCFC-124 are fed at 180° C. thus performing a contact time of 30 seconds.

The products are analysed by gaschromatography and contain:
125: 32.5% by moles; 124: 31.7% by moles;
123: 35.2% by moles; others: 0.6% by moles.

This time the analysis is carried out with a more sensitive instrument and 115 in 125 was evaluated as 0.002% by weight.

EXAMPLE 4

Example 1 was repeated but by utilizing a temperature of 240° C. and a contact time of 10 seconds by halving the 124 feeding.

The products are analysed by gaschromatography and contain:
125: 24.5% by moles; 124: 50.3% by moles;
123: 24.8% by moles; others: 0.4% by moles.

115 in 125 is below the limit of 0.005% by weight.

EXAMPLE 5 (comparative)

250 cc of the catalyst prepared according to example 1 except that the final calcination was carried out in nitrogen flow instead of in air, were placed in the reactor utilized in the previous examples.

At 280° C. and at a pressure slightly higher than the atmospheric one, 180 g of 124 diluted with 25 Nl/hour of nitrogen were fed, contact time of 10 seconds and the following products were obtained which were analysed by gascchromatography.

125: 36.7% by moles; 124: 32.56 by moles;
123a: lower than 0.05% by moles;
123: 27.8% by moles; others: 2.8% by moles.

115 in 125 is higher than 0.1% by weight.

I claim:

1. Process for preparing pentafluoroethane containing amounts of 1-chloropentafluoroethane lower than 0.02% by weight wherein pentafluoroethane is obtained by a disputation process of tetrafluorochloroethane $CF_3CHClF$ in gaseous phase in the presence of a chromium oxide catalyst of the formula $Cr_2O_3$ supported on a support comprising $AlF_3$, said support having a content in fluorine corresponding to at least 90% of $AlF_3$ determined on the total weight of the support, wherein temperatures are selected to be from 140°–180° C. for contact times comprised between 15–30 seconds, from 180° to 240° C. for contact times between 5 to 15 seconds, from 240° to 260° C. for contact times between 1 to 5 seconds, from 260° to 300° C. for contact times between 0.1 to 1 second, and subsequent separation from the obtained products.

2. Process according to claim 1, wherein the temperature ranges from 160° C. to 260° C.

3. Process according to claim 1, wherein the temperature ranges from 180° C. to 240° C.

4. Process according to claim 1, wherein the catalyst support consists of 100% by weight $AlF_3$ comprising in admixture the beta, gamma and/or delta forms.

5. Process according to claim 4, wherein the supported chromium catalyst of the formula $Cr_2O_3$ is prepared by impregnation of $AlF_3$ with an aqueous solution of a trivalent chrome salt and subsequent treatment, upon drying, with air or nitrogen at temperatures from 200° to 600° C.

6. Process according to claim 5, wherein the treatment is carried out with air at temperatures from 350° C. to 500° C.

7. Process according to claim 1, wherein the dismutation reaction is carried out on a fluidized bed.

* * * * *

UNITED STATES PATENT AND TRADEMARK OFFICE
CERTIFICATE OF CORRECTION

PATENT NO.   : 5,841,006
DATED        : November 24, 1998
INVENTOR(S)  : Paolo Cuzzato It is certified that error appears in the above-identified patent and that said Letters Patent is hereby corrected as shown below:

In claim 1, column 4, lines 17-18, "disputation" should read --dismutation--.

Signed and Sealed this

Twenty-third Day of March, 1999

Attest:

Q. TODD DICKINSON

Attesting Officer

Acting Commissioner of Patents and Trademarks